US007000271B2

(12) United States Patent
Varadharajulu

(10) Patent No.: US 7,000,271 B2
(45) Date of Patent: Feb. 21, 2006

(54) TABLE CONTROL METHOD AND TABLE SYSTEM

(75) Inventor: Muthuvelan Varadharajulu, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/704,837

(22) Filed: Nov. 10, 2003

(65) Prior Publication Data

US 2004/0172145 A1 Sep. 2, 2004

(30) Foreign Application Priority Data

Nov. 12, 2002 (JP) .............................. 2002-327795

(51) Int. Cl.
  *A61G 13/04* (2006.01)
  *A61B 6/04* (2006.01)
(52) U.S. Cl. ...................... 5/610; 5/611; 5/943; 5/601; 378/209
(58) Field of Classification Search .................. 5/607, 5/608, 610, 611, 601, 600, 11, 943; 378/209
  See application file for complete search history.

(56) References Cited

U.S. PATENT DOCUMENTS

| 3,997,926 | A |   | 12/1976 | England |
| 4,481,657 | A | * | 11/1984 | Larsson ...................... 378/209 |
| 4,761,000 | A |   | 8/1988  | Fisher et al. |
| 4,842,259 | A | * | 6/1989  | Rice ............................... 5/601 |
| 5,013,018 | A | * | 5/1991  | Sicek et al. ..................... 5/601 |
| 5,014,292 | A | * | 5/1991  | Siczek et al. ................ 378/196 |
| 5,131,105 | A |   | 7/1992  | Harrawood et al. |
| 5,205,004 | A |   | 4/1993  | Hayes et al. |
| 6,094,760 | A | * | 8/2000  | Nonaka et al. ................. 5/601 |
| 6,353,949 | B1 |   | 3/2002 | Falbo |
| 6,651,279 | B1 | * | 11/2003 | Muthuvelan .................... 5/600 |
| 6,857,147 | B1 | * | 2/2005 | Somasundaram ............... 5/601 |
| 6,935,780 | B1 | * | 8/2005 | Barde et al. ................. 378/209 |
| 2004/0098804 | A1 | * | 5/2004 | Varadharajulu et al. ........ 5/611 |
| 2004/0172756 | A1 | * | 9/2004 | Somasundaram ............... 5/600 |
| 2004/0172757 | A1 | * | 9/2004 | Somasundaram ............... 5/601 |
| 2004/0172758 | A1 | * | 9/2004 | Alakkat ......................... 5/610 |
| 2005/0084074 | A1 | * | 4/2005 | Varadharajulu ............. 378/209 |
| 2005/0114996 | A1 | * | 6/2005 | Somasundaram ............... 5/601 |

* cited by examiner

*Primary Examiner*—Robert G. Santos
(74) *Attorney, Agent, or Firm*—Carl B. Horton, Esq.; Armstrong Teasdale LLP

(57) ABSTRACT

For the purpose of providing a method of keeping an iso-center at a fixed position regardless of the tilt of a table top, and a table system having such a function, an apparatus comprises a table top member; lifting means for moving the table top member up and down; forwarding/backing means for longitudinally moving the table top member forward and backward; tilting means for tilting the table top member from a horizontal state; and control means, and the table top member is tilted around an iso-center lying at a spatial position different from a mechanical center of tilt motion of the table top member by the control means controlling vertical displacement of the mechanical center and longitudinal displacement of the table top member according to a tilt angle.

8 Claims, 3 Drawing Sheets

TABLE CONTROL METHOD AND TABLE SYSTEM

CROSS REFERENCE TO RELATED APPLICATIONS

This application claims the benefit of Japanese Application No. 2002-327795 filed Nov. 12, 2002.

BACKGROUND OF THE INVENTION

The present invention relates to a table control method and table system, and more particularly to a method of tilting a table from a horizontal state, and a table system that can be tilted from a horizontal state.

In a conventional medical image capturing apparatus such as an X-ray imaging apparatus, a table system for supporting a subject to be imaged lying thereon is employed. Such table systems include one having a table top that can be arbitrarily tilted from a horizontal state (see, for example, Patent Document 1).

[Patent Document 1]
Specification and drawings of U.S. Pat. No. 6,353,949B1 (Columns 5–6, FIGS. 1–4).

When a desired region in the subject is imaged in the horizontal state and then the same region is imaged with a different tilt of the table top, the center of imaging, i.e., the iso-center, must lie at the same position. However, when the tilt of the table top is changed the iso-center is moved in the aforementioned table system, so that readjustment is required.

SUMMARY OF THE INVENTION

It is therefore an object of the present invention to provide a method of keeping the iso-center at a fixed position regardless of the tilt of the table top, and a table system having such a function.

(1) The present invention, in one aspect thereof for solving the aforementioned problem, is a table control method for tilting a table top from a horizontal state, characterized in comprising: tilting the table top around one point lying at a spatial position different from a mechanical center of tilt motion of the table top by controlling vertical displacement of the mechanical center and longitudinal displacement of the table top according to a tilt angle.

(2) The present invention, in another aspect thereof for solving the aforementioned problem, is a table system, characterized in comprising: a table top member; lifting means for moving the table top member up and down; forwarding/backing means for longitudinally moving the table top member forward and backward; tilting means for tilting the table top member from a horizontal state; and control means for tilting the table top member around one point lying at a spatial position different from a mechanical center of tilt motion of the table top member by controlling vertical displacement of the mechanical center and longitudinal displacement of the table top member according to a tilt angle.

In the invention of these aspects, since the table top is tilted around one point lying at a spatial position different from a mechanical center of tilt motion of the table top by controlling vertical displacement of the mechanical center and longitudinal displacement of the table top according to a tilt angle, the iso-center can be kept at a fixed position regardless of the tilt of the table top.

When horizontal and vertical distances between the aforesaid mechanical, center and the aforesaid one point in the horizontal state of the table top are represented by Ch and Cv, respectively, and a target value of the tilt angle is represented by $\phi 1$, the amount of the vertical displacement of the mechanical center is preferably defined as:

$$Y1 = \{(-1 * \mathrm{Sqrt}(Ch^2 + Cv^2)) * \quad \text{[Equation 7]}$$
$$(\mathrm{Sin}\,\phi 1 / \mathrm{Sin}((180 - \mathrm{Abs}(\phi 1))/2)) *$$
$$\mathrm{Sin}(90 + \mathrm{Abs}(\phi 1/2)) -$$
$$\mathrm{Sin}^{-1}(Cv / \mathrm{Sqrt}(Ch^2 + Cv^2))))\} +$$
$$\{(-1 * \mathrm{Sqrt}(Ch^2 + Cv^2)) *$$
$$(\mathrm{Sin}\,\phi 1 / \mathrm{Sin}((180 - \mathrm{Abs}(\phi 1))/2)) *$$
$$\mathrm{Sqrt}(1 - (\mathrm{Sin}(90 + \mathrm{Abs}(\phi 1/2) -$$
$$\mathrm{Sin}^{-1}(Cv / \mathrm{Sqrt}(Ch^2 + Cv^2)))^2) * \mathrm{Tan}\,\phi 1\},$$

and the amount of the longitudinal displacement of the table top is preferably defined as:

$$Y3 = (-1*\mathrm{Sqrt}(Ch^2+Cv^2))*(\mathrm{Sin}\ \phi 1/\mathrm{Sin}((180-\mathrm{Abs}(\phi 1))/2))*\mathrm{Sqrt}(1-(\mathrm{Sin}(90+\mathrm{Abs}(\phi 1/2)-\mathrm{Sin}^{-1}(Cv/\mathrm{Sqrt}(Ch^2+Cv^2))))^2)/\mathrm{Cos}\ \phi 1, \quad \text{[Equation 8]}$$

so that accuracy of keeping of the iso-center may be improved.

When distances between the aforesaid mechanical center and a point of action and a fulcrum of an actuator, which has the point of action and fulcrum that move up and down along with the mechanical center for tilting the table top by extension/contraction of its length, are represented by C5 and C6, respectively, the length of the actuator in the horizontal state of the table top is represented by C7, and an angle at the mechanical center subtending the point of action and the fulcrum in the horizontal state of the table top is represented by $\phi 2$, an amount-of change in the length of the actuator is preferably defined as:

$$Y4 = \{\mathrm{Sqrt}((C6-(C5*\mathrm{Cos}(\phi 2-\phi 1)))^2 + (C5*\mathrm{Cos}(\phi 2-\phi 1))^{\ 2})\} - C7, \quad \text{[Equation 9]}$$

so that accuracy of tilting of the table top may be improved.

The longitudinal displacement of the table top is preferably defined within predetermined limits so that a mechanism for the displacement may be simplified.

Therefore, the present invention provides a method of keeping the iso-center at a fixed position regardless of the tilt of the table top, and a table system having such a function.

Further objects and advantages of the present invention will be apparent from the following description of the preferred embodiments of the invention as illustrated in the accompanying drawings.

DETAILED DESCRIPTION OF THE INVENTION

Figure 1:
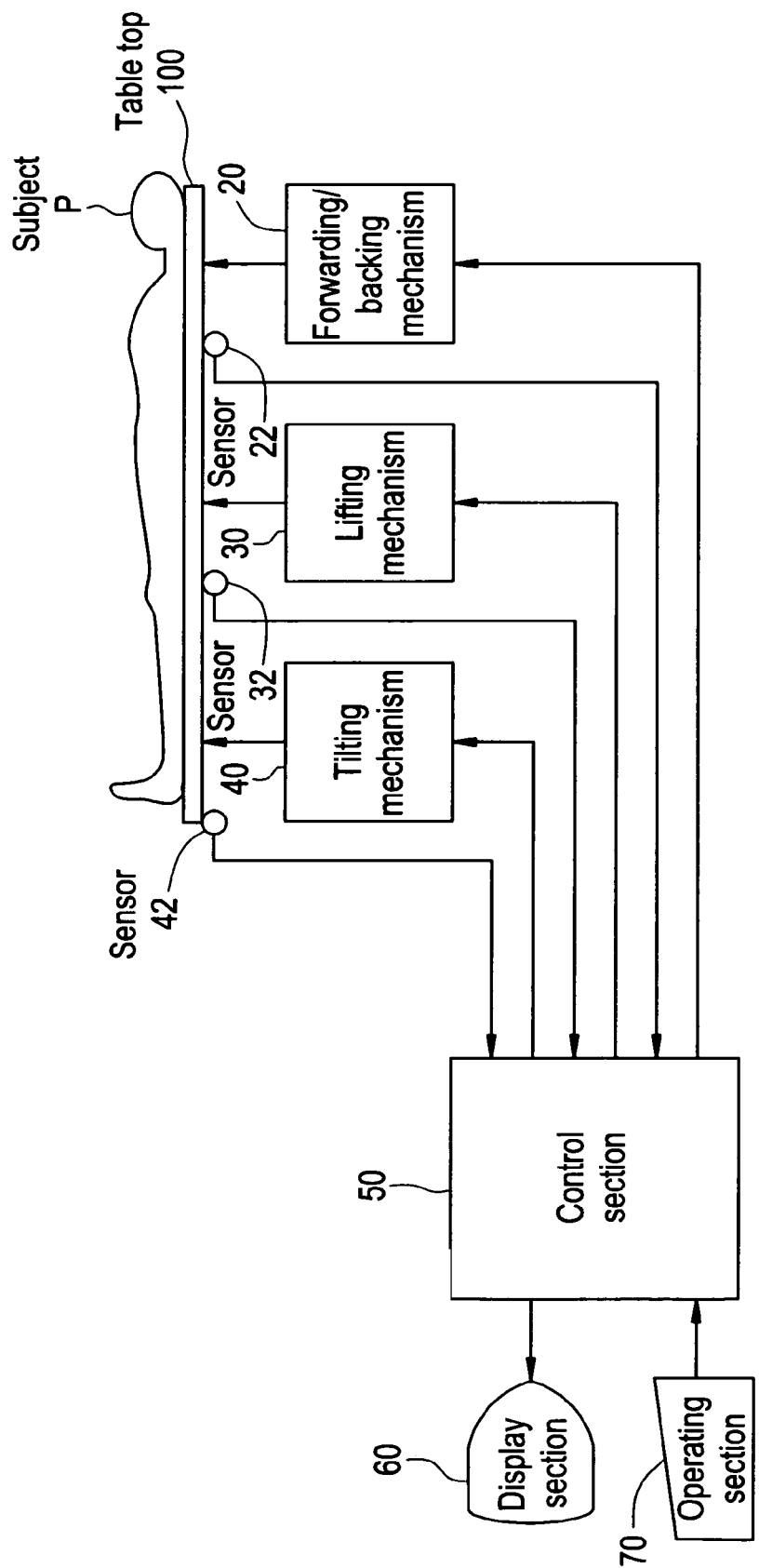
FIG. 1 is a block diagram of an apparatus in accordance with one embodiment of the present invention.

Embodiments of the present invention will now be described in detail with reference to the accompanying drawings. FIG. 1 shows a block diagram of a table system. The apparatus is an embodiment of the present invention. The configuration of the apparatus represents an embodiment of the apparatus of the present invention. The operation of the apparatus represents an embodiment of the method of the present invention.

As shown in FIG. 1, the present apparatus comprises a table top 100. A subject P is rested on the table top 100 in a supine position. The table top 100 is driven by a forwarding/backing mechanism 20, a lifting mechanism 30, and a tilting mechanism 40 to allow longitudinal forward/backward movement, vertical up/down movement, and tilting with respect to a horizontal direction, respectively. The forward/backward movement, up/down movement and tilting of the table top 100 are detected by sensors 22, 32 and 42, respectively.

The table top 100 is an embodiment of the table top member of the present invention. The forwarding/backing mechanism 20 is an embodiment of the forwarding/backing means of the present invention. The lifting mechanism 30 is an embodiment of the lifting means of the present invention. The tilting mechanism 40 is an embodiment of the tilting means of the present invention.

The forwarding/backing mechanism 20, lifting mechanism 30 and tilting mechanism 40 are controlled by a control section 50. Detected signals from the sensors 22, 32 and 42 are input to the control section 50. For the control section 50, a computer is employed, for example. The control section 50 is an embodiment of the control means of the present invention.

The control section 50 is connected with a display section 60 and an operating section 70. The display section 60 and operating section 70 are used by an operator to interactively operate the present apparatus.

Figure 2:
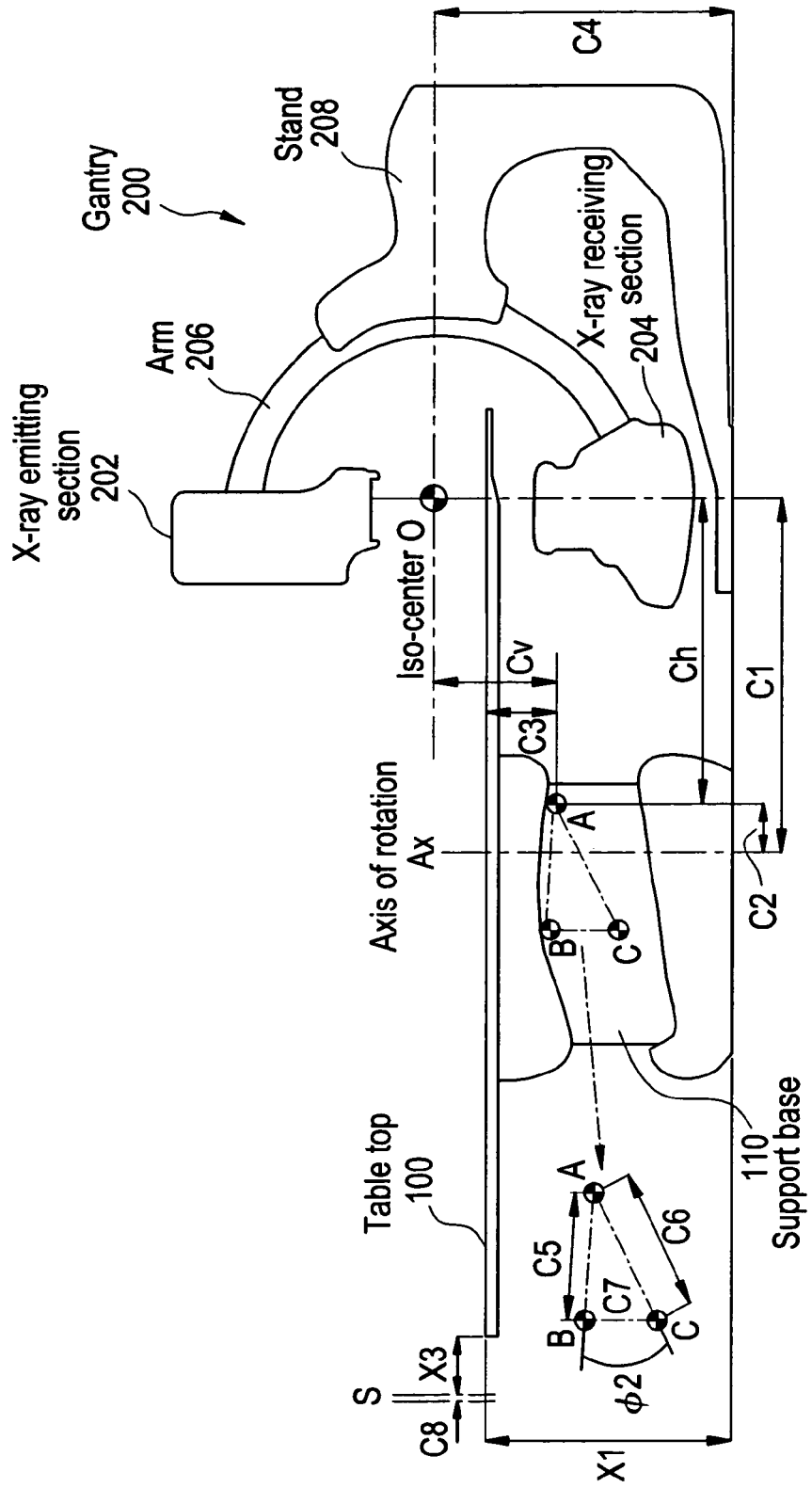
FIG. 2 shows a horizontal state of a table top.

FIG. 2 shows a schematic configuration of the present apparatus along with a gantry for X-ray imaging. As shown, a gantry 200 supports an X-ray emitting section 202 and an X-ray receiving section 204 that face each other, by an arc-shaped arm 206. The arm 206 is supported by a stand 208.

The gantry 200 has an iso-center O in a space between the X-ray emitting section 202 and the X-ray receiving section 204. The iso-center O corresponds to a center of the arc of the arm 206. By moving the arm 206 along the arc by a feed mechanism incorporated in the stand 208, the X-ray emitting section 202 and the X-ray receiving section 204 rotate around the iso-center O while maintaining their facing relationship. The iso-center O lies at a height C4 from the floor.

The table top 100 is supported by a support base 110. In FIG. 2, a horizontal state of the table top 100 is shown. The support base 110 incorporates therein the forwarding/backing mechanism 20, lifting mechanism 30, tilting mechanism 40, and sensors 22, 32 and 42 shown in FIG. 1. The control section 50, display section 60 and operating section 70 are housed in a console (not shown), which is installed at an appropriate position, such as in an operator room.

The support base 110 has an axis of rotation AX of the table top 100. The table top 100 is allowed to rotate around the axis of rotation AX in a horizontal plane. The position of the support base 110 is represented by the position of the axis of rotation AX. The support base 110 lies at a horizontal distance C1 from the iso-center O of the gantry 200.

The height of the table top 100 from the floor is X1. The height X1 changes with up/down movement of the table top 100. The table top 100 is at a state of being moved forward by a distance X3 from a reference position S toward the gantry 200. The movement toward the gantry will be referred to as forward movement, and movement away from the gantry as backward movement hereinbelow.

The distance allowed for backward movement from the reference position S is limited to C8. Therefore, the maximum distance allowed for backward movement from the state of the table top 100 being moved forward by a distance X4 from the reference position, as shown, is X3+C8.

A schematic configuration of the tilting mechanism 40 in the support base 110 is indicated by a triangle ABC. The vertex A represents a mechanical center of tilting movement of the table top 100. The vertex B represents a point of action of driving force of an actuator for the tilting mechanism 40. The vertex C represents a fulcrum of the actuator.

The actuator is one that is extendable in length, such as an electromotive ball screw, and its extension and contraction change the distance between the fulcrum C and point of action B, thereby tilting the table top 100 around A. The lifting mechanism 30 moves up/down such a tilting mechanism 40 and forwarding/backing mechanism 20 along with the table top 100.

In the tilting mechanism 40, the distance between A and B is C5, and that between A and C is C6. If the table top 100 remains in the horizontal state, the distance between B and C is C7, and an angle at the mechanical center A subtending the point of action B and fulcrum C is $\phi 2$.

The mechanical center A lies at a horizontal distance C2 from the axis of rotation AX toward the gantry 200. The distance from the mechanical center A to the surface of the table top 100 is C3. Thus, the mechanical center A lies at a horizontal distance Ch and at a vertical distance Cv from the iso-center O. Ch and Cv are given by the following formulae, respectively:

$$Ch = C1 - C2, \text{ and} \qquad \text{[Equation 10]}$$

$$Cv = C4 - X1 + C3. \qquad \text{[Equation 11]}$$

Figure 3:
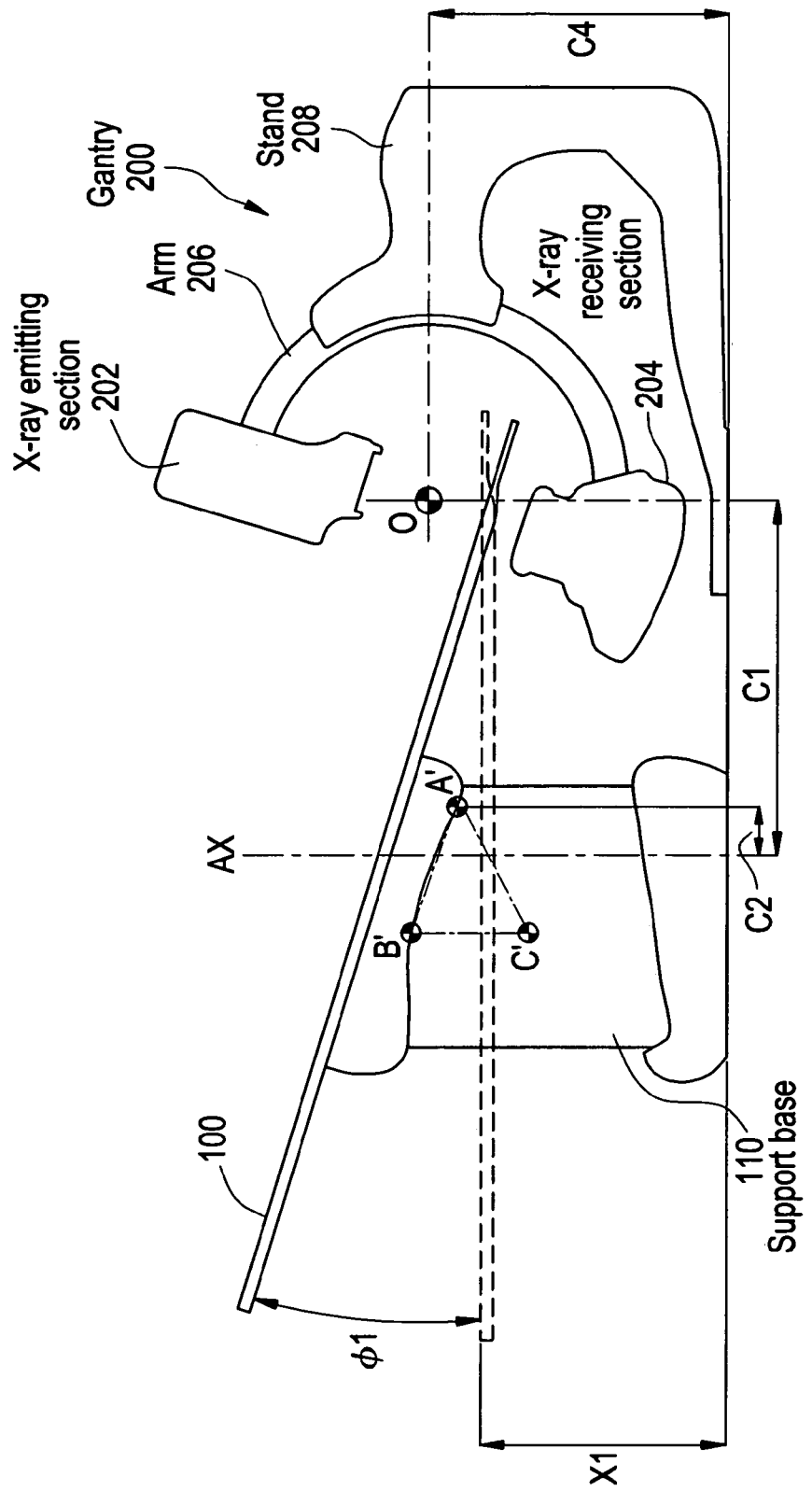
FIG. 3 shows a tilt state of the table top.

FIG. 3 shows a state in which the table top 100 is tilted. The tilt angle is $\phi 1$. This state corresponds to a case in which imaging is conducted with the head of the subject slightly lowered in angiography of the head, for example.

In such a condition, although the tilting of the table top 100 is tilting around the mechanical center A from the mechanical viewpoint, it is achieved as tilting around the iso-center O from the geometrical viewpoint. Specifically, tilting of the table top 100 is conducted so that the tilting will not change the length and the position in the table top 100 of a perpendicular dropped from the iso-center O and meeting with the table top 100 in the horizontal state.

To enable such tilting, the control section 50 controls the tilting means 40 to tilt the table top 100 around the mechanical center A, and also controls the lifting mechanism 30 and forwarding/backing mechanism 20 to change the vertical position of the mechanical center A and the position of the table top 100 in the forward/backing direction according to the tilt angle $\phi 1$.

The control section 50 calculates an amount of change Y1 in the vertical position of the mechanical center A by the formula below, and controls the lifting mechanism 30 to make the amount of change in the vertical position of the mechanical center A agree with Y1:

$$Y1 = \{(-1*\text{Sqrt}(Ch^2 + Cv^2))* \quad \text{[Equation 12]}$$
$$(\text{Sin}\phi 1/\text{Sin}((180 - \text{Abs}(\phi 1))/2))*$$
$$\text{Sin}(90 + \text{Abs}(\phi 1/2) -$$
$$\text{Sin}^{-1}(Cv/\text{Sqrt}(Ch^2 + Cv^2))))\} +$$
$$\{(-1*\text{Sqrt}(Ch^2 + Cv^2))*$$
$$(\text{Sin}\phi 1/\text{Sin}((180 - \text{Abs}(\phi 1))/2))*$$
$$\text{Sqrt}(1 - (\text{Sin}(90 + \text{Abs}(\phi 1/2) -$$
$$\text{Sin}^{-1}(Cv/\text{Sqrt}(Ch^2 + Cv^2))))^2)*\text{Tan}\phi 1\}.$$

The control section 50 also calculates an amount of change Y3 in the position of the table top 100 in the forwarding/backing direction by the formula below, and controls the forwarding/backing mechanism 20 to make the amount of change in the position of the table top 100 in the forward/backing direction agree with Y3:

$$Y3=(-1*\text{Sqrt}(Ch^2+Cv^2))*(\text{Sin } \phi 1/\text{Sin }((180-\text{Abs}(\phi 1))/2))*\text{Sqrt}(1-(\text{Sin}(90+\text{Abs}(\phi 1/2)-\text{Sin}^{-1}(Cv/\text{Sqrt}(Ch^2+Cv^2))))^2)/\text{Cos } \phi 1. \quad \text{[Equation 13]}$$

The control section 50 further calculates an amount of change Y4 in the length of the actuator for tilting the table top 100 up to the tilt angle φ1 by the formula below, and controls the actuator to make the amount of change in the length of the actuator agree with Y4:

$$Y4=\{\text{Sqrt}((C6-(C5*\text{Cos}(\phi 2-\phi 1)))^2+(C5*\text{Cos}(\phi 2-\phi 1))^2)\}-C7. \quad \text{[Equation 14]}$$

In the formulae, the sign of the tilt angle φ1 is defined as (+) for a tilt in a direction of lifting up of an end of the table top 100 adjacent to, the gantry 200, and as (−) for a tilt in a direction of lowering. The sign of Y1 is defined as (+) in a direction of lifting up of the table top 100, and as (−) in a direction of lowering. The sign of Y3 is defined as (+) in a direction of backward movement of the table top 100, and as (−) in a direction of forward movement. The sign of Y4 is defined as (+) in a direction of extension of the actuator, and as (−) in a direction of contraction.

To calculate Y1, Y3 and Y4 by the formulae above, the tilt angle φ1 of the table top 100 is input to the control section 50 by a user via the operating section 70. Moreover, the horizontal distance Ch and vertical distance Cv between the mechanical center A and iso-center O are input to the control section 50 by the user via the operating section 70. However, values that are directly input are fixed values C1, C2, C3 and C4 that are known beforehand, and Ch and Cv are calculated by the control section 50 using the formulae (10) and (11), respectively, from those fixed values and the detected height value X1 of the table top 100 in the horizontal state.

By such control based on Y1, Y3 and Y4, the table top 100 can be tilted around the iso-center O. Thus, within the subject laid on the table 100, the position of the iso-center O can be prevented from changing from the horizontal state of the table top 100. Therefore, imaging can be conducted with the imaging center always kept the same regardless of tilt.

If the value of Y3 obtained by calculation is larger than the maximum value X3+C8 allowed for backward movement, the value of Y3 is set to X3+C8 regardless of the calculated value. This prevents excessive force from being applied to a stopper, for example, in attempting to move the table top 100 beyond the maximum value allowed for backward movement. Moreover, configuration of the forwarding/backing mechanism 20 can be simplified.

Many widely different embodiments of the invention may be configured without departing from the spirit and the scope of the present invention. It should be understood that the present invention is not limited to the specific embodiments described in the specification, except as defined in the appended claims.

The invention claimed is:

1. A table control method for tilting a table top from a horizontal state, comprising:
   tilting the table top around one point including an iso-center lying at a spatial position different from a mechanical center of tilt motion of the table top by controlling vertical displacement of the mechanical center and longitudinal displacement of the table top according to a tilt angle and by controlling a tilting mechanism tilting the table top; and
   the tilting mechanism separate from a lifting mechanism controlling the vertical displacement and from a mechanism controlling the longitudinal displacement.

2. The table control method of claim 1, wherein the longitudinal displacement of the table top is defined within predetermined limits.

3. A table control method for tilting a table top from a horizontal state, comprising:
   tilting the table top around one point including an iso-center lying at a spatial position different from a mechanical center of tilt motion of the table top by controlling vertical displacement of the mechanical center and longitudinal displacement of the table top according to a tilt angle and by controlling a tilting mechanism tilting the table top, wherein when horizontal and vertical distances between said mechanical center and said one point in the horizontal state of the table top are represented by Ch and Cv, respectively, and a target value of the tilt angle is represented by φ1, the amount of the vertical displacement of the mechanical center is defined as:

$$Y1 = \{(-1*\text{Sqrt}(Ch^2 + Cv^2))*(\text{Sin}\phi 1/\text{Sin}((180 - \text{Abs}(\phi 1))/2))*$$
$$\text{Sin}(90 + \text{Abs}(\phi 1/2) - \text{Sin}^{-1}(Cv/\text{Sqrt}(Ch^2 + Cv^2))))\} +$$
$$\{(-1*\text{Sqrt}(Ch^2 + Cv^2))*(\text{Sin}\phi 1/\text{Sin}((180 - \text{Abs}(\phi 1))/2))*$$
$$\text{Sqrt}(1 - (\text{Sin}(90 + \text{Abs}(\phi 1/2) -$$
$$\text{Sin}^{-1}(Cv/\text{Sqrt}(Ch^2 + Cv^2))))^2)*\text{Tan}\phi 1\},$$

and the amount of the longitudinal displacement of the table top is defined as:

$$Y3=(-1*\text{Sqrt}(Ch^2Cv^2))*(\text{Sin }\phi 1/\text{Sin}((180-\text{Abs}(\phi 1))/2))*\text{Sqrt}(1-(\text{Sin}(90+\text{Abs}(\phi 1/2)-\text{Sin}^{-1}(Cv/\text{Sqrt}(Ch^2+Cv^2))))^2)/\text{Cos } \phi 1.$$

4. The table control method of claim 3, wherein when distances between said mechanical center and a point of action and a fulcrum of an actuator, which has the point of action and fulcrum that move up and down along with said mechanical center for tilting the table top by extension/contraction of a length of the actuator, are represented by C5 and C6, respectively, the length of the actuator in the horizontal state of the table top is represented by C7, and an angle at said mechanical center subtending said point of action and said fulcrum in the horizontal state of the table top is represented by $\phi 2$, an amount of change in the length of the actuator is defined as:

$$Y4=\{Sqrt((C6-(C5*Cos(\phi 2-\phi 1)))^2+(C5*Cos(\phi 2 -\phi 1))^{\,2})\}-C7.$$

5. A table system, comprising:
   a table top member;
   a lifting device for moving the table top member up and down;
   a forwarding/backing device for longitudinally moving the table top member forward and backward;
   a tilting device for tilting the table top member from a horizontal state; and
   a control device for tilting the table top member around one point including an isocenter lying at a spatial position different from a mechanical center of tilt motion of the table top member by controlling vertical displacement of the mechanical center and longitudinal displacement of the table top member according to a tilt angle and by controlling said tilting device, and the tilting device separate from a lifting mechanism controlling the vertical displacement and from a mechanism controlling the longitudinal displacement.

6. The table system of claim 5, wherein the control device defines the longitudinal displacement of the table top member within predetermined limits.

7. A table system comprising:
   a table top member;
   a lifting device for moving the table top member up and down;
   a forwarding/backing device for longitudinally moving the table top member forward and backward;
   a tilting device for tilting the table top member from a horizontal state; and
   a control device for tilting the table top member around one point including an isocenter lying at a spatial position different from a mechanical center of tilt motion of the table top member by controlling vertical displacement of the mechanical center and longitudinal displacement of the table top member according to a tilt angle and by controlling said tilting device, wherein when horizontal and vertical distances between said mechanical center and said one point in the horizontal state of the table top member are represented by Ch and Cv, respectively, and a target value of the tilt angle is represented by $\phi 1$, the control device defines the amount of the vertical displacement of the mechanical center as:

$$Y1 = \{(-1*Sqrt(Ch^2 + Cv^2))*(Sin\phi 1/Sin((180-Abs(\phi 1))/2))*$$
$$Sin(90 + Abs(\phi 1/2) - Sin^{-1}(Cv/Sqrt(Ch^2 + Cv^2))))\} +$$
$$\{(-1*Sqrt(Ch^2 + Cv^2))*(Sin\phi 1/Sin((180-Abs(\phi 1))/2))*$$
$$Sqrt(1 - (Sin(90 + Abs(\phi 1/2) -$$
$$Sin^{-1}(Cv/Sqrt(Ch^2 + Cv^2))))^2)*Tan\phi 1\},$$

and the amount of the longitudinal displacement of the table top member as:

$$Y3=(-1*Sqrt(Ch^2+Cv^2))*(Sin\phi 1/Sin((180-Abs(\phi 1))/2))$$

8. The table system of claim 7, wherein
   the tilting device has an actuator having a point of action and a fulcrum that move up and down along with said mechanical center for tilting the table top member by extension/contraction of a length of the actuator; and
   when distances between said mechanical center and said point of action and said fulcrum are represented by C5 and C6, respectively, the length of the actuator in the horizontal state of the table top member is represented by C7, and an angle at said mechanical center subtending said point of action and said fulcrum in the horizontal state of the table top member is represented by $\phi 2$, an amount of change in the length of the actuator is defined as:

$$Y4=\{Sqrt((C6-(C5*Cos(\phi 2-\phi 1)))^2+ C5*Cos(\phi 2-\phi 1)C5*Cos(\phi 2-\phi 1)^2)\}-C7.$$

* * * * *